United States Patent
Park et al.

(10) Patent No.: US 11,408,725 B2
(45) Date of Patent: Aug. 9, 2022

(54) THREE-DIMENSIONAL OPTICAL TOMOGRAPHY METHOD AND APPARATUS USING PARTIALLY COHERENT LIGHT AND MULTI-ILLUMINATION PATTERN

(71) Applicant: Tomocube, Inc., Daejeon (KR)

(72) Inventors: YongKeun Park, Daejeon (KR); Herve Jerome Hugonnet, Daejeon (KR)

(73) Assignee: Tomocube, Inc., Daejeon (KR)

( * ) Notice: Subject to any disclaimer, the term of this patent is extended or adjusted under 35 U.S.C. 154(b) by 0 days.

(21) Appl. No.: 17/024,303

(22) Filed: Sep. 17, 2020

(65) Prior Publication Data
US 2022/0034646 A1 Feb. 3, 2022

(30) Foreign Application Priority Data
Jul. 28, 2020 (KR) .................. 10-2020-0093713

(51) Int. Cl.
*G01B 9/02* (2022.01)
*G01B 9/02091* (2022.01)
(Continued)

(52) U.S. Cl.
CPC ...... *G01B 9/02091* (2013.01); *G01B 11/2441* (2013.01); *G01B 11/254* (2013.01)

(58) Field of Classification Search
CPC ............ G01B 9/02091; G01B 9/02034; G01B 11/2441; G01B 11/254
See application file for complete search history.

(56) References Cited

U.S. PATENT DOCUMENTS

| 5,671,085 A | 9/1997 | Gustafsson |
| 7,535,607 B2 | 5/2009 | Schwerdtner |
| (Continued) | | |

FOREIGN PATENT DOCUMENTS

| JP | 2009-223348 A | 10/2009 |
| KR | 101263968 B1 | 5/2013 |
| KR | 101888924 B1 | 8/2018 |

OTHER PUBLICATIONS

Rodrigo, J. A. et al., "Fast label-free optical diffraction tomography compatible with conventional wide-field microscopes", Enhanced and Synthetic Vision 2003: [Conference Enhanced and Synthetic Vision 2002]; Apr. 21, 2003, Orlando, FL [Proceedings of SPIE ISSN 0277-786X], SPIE, vol. 11060, pp. 1106016-1106016, Jun. 21, 2019.
(Continued)

*Primary Examiner* — Tarifur R Chowdhury
*Assistant Examiner* — Jonathon Cook
(74) *Attorney, Agent, or Firm* — Nixon Peabody LLP

(57) ABSTRACT

Proposed are a three-dimensional (3D) optical tomography method and apparatus using a partially coherent light and a multi-illumination pattern. The 3D optical diffraction tomography method based on low coherence light and a multi-illumination pattern using a 3D optical diffraction tomography apparatus may include making light incident on a sample using a plurality of patterns, measuring, by an image measurement unit, different locations at different depth locations of the sample and measuring two-dimensional (2D) images of the sample, and reconstructing 3D refractive index information of the sample based on the different patterns and the 2D images obtained at the different depth locations.

8 Claims, 11 Drawing Sheets

(51) Int. Cl.
    *G01B 11/24*    (2006.01)
    *G01B 11/25*    (2006.01)

(56)  References Cited

U.S. PATENT DOCUMENTS

| | | | | |
|---|---|---|---|---|
| 9,626,587 | B2* | 4/2017 | Shi | G06K 9/52 |
| 9,955,863 | B2* | 5/2018 | Frisken | G06T 11/008 |
| 10,082,662 | B2* | 9/2018 | Park | G02B 21/367 |
| 10,665,001 | B2* | 5/2020 | Horstmeyer | G02B 27/58 |
| 2002/0191193 | A1* | 12/2002 | Smirnov | G01N 21/45 |
| | | | | 356/517 |

OTHER PUBLICATIONS

Bailleul, J. et al., "3D high- and isotropic resolution in tomographic diffractive microscopy by illumination angular scanning, specimen rotation and improved data recombination", Proceedings of SPIE; [Proceedings of SPIE ISSN 0277-786x vol. 10524], SPIE, vol. 9896, pp. 98960M-98960M, Apr. 29, 2016.

Park, C. et al., "Generalized quantification of three-dimensional resolution in optical diffraction tomography using the projection of maximal spatial bandwidths", arxiv.org, Cornell University Library, Ithaca, NY, Jun. 4, 2018.

Li, J. et al., "Three-dimensional tomographic microscopy technique with multi-frequency combination with partially coherent illuminations", Progress in Biomedical Optics and Imaging, SPIE—International Society for Optical Engineering, Bellingham, WA, US, vol. 10887, pp. 108870O-108870O, Mar. 4, 2019.

Li, J. et al., "Computational microscopy for quantitative phase imaging and refractive index tomography using annular illumination", Progress in Biomedical Optics and Imaging, SPIE—International Society for Optical Engineering, Bellingham, WA, US, vol. 11249, pp. 112491F-112491F, Feb. 14, 2020.

Extended European Search Report in European Patent Application No. EP 20204594.4, dated Mar. 30, 2021 (10 pages).

Streibl, N., "Three-dimensional imaging by a microscope." Josa A 2(2): 121-127 (1985).

Bao, Y. & Gaylord, T.K., "Quantitative phase imaging method based on an analytical nonparaxial partially coherent phase optical transfer function." Josa A , 33(11): 2125-2136 (2016).

Soto, J.M. et al., "Label-free quantitative 3D tomographic imaging for partially coherent light microscopy," Optics Express, 25(14): 15699-15712 (2017).

Park, Y. et al., "Quantitative phase imaging in Biomedicine," Nature Photonics 12, pp. 578-589 (2018).

\* cited by examiner

THREE-DIMENSIONAL OPTICAL TOMOGRAPHY METHOD AND APPARATUS USING PARTIALLY COHERENT LIGHT AND MULTI-ILLUMINATION PATTERN

CROSS REFERENCE TO RELATED APPLICATION

This application claims priority under 35 U.S.C. § 119 to Korean Patent Application No. 10-2020-0093713 filed on Jul. 28, 2020, which is incorporated herein by reference in its entirety.

BACKGROUND OF THE INVENTION

1. Technical Field

The following embodiments relate to a three-dimensional (3D) optical tomography method and apparatus using a partially coherent light and a multi-illumination pattern and, more particularly, to a 3D optical diffraction tomography method and apparatus for restoring a 3D refractive index image using low coherence light (or partially coherent light).

2. Description of the Related Art

Optical diffraction tomography (ODT) can be used to quantitatively restore a refractive index (RI) distribution of a sample using a noninvasive method, and is thus applied to various fields, such as checking a defect in a plastic lens and measuring a fine 3D temperature distribution, in addition to biological research of bacteria, a cell or a tissue (e.g., Non-Patent Document 1).

The existing ODT is based on measuring and analyzing, using interferometry, a pattern generated through coherence between a signal, scattered from a sample, and a reference beam based on high coherent light. However, in this case, image quality degradation, such as speckle noise, may occur due to high coherence of the light. Furthermore, several weak points (e.g., noise attributable to vibration, a complicated machine, and requirements for maintaining precise equipment) occur in a process of configuring and maintaining interferometry.

In order to solve such a problem, a theory capable of measuring refractive index information of a sample using low coherence light (or partially coherent light) was developed (e.g., Non-Patent Documents 2 and 3), and was recently experimentally implemented (e.g., Non-Patent Document 4). However, a 3D refractive index image obtained using the conventional method does not accurately measure a 3D structure of a sample and is subjected to significant image distortion.

PRIOR ART DOCUMENT

Non-Patent Document (Non-Patent Document 1) Park, YongKeun, Christian Depeursinge, and Gabriel Popescu. "Quantitative phase imaging in biomedicine." Nature Photonics 12.10 (2018): 578-589.

(Non-Patent Document 2) Streibl, Norbert. "Three-dimensional imaging by a microscope." JOSA A 2.2(1985): 121-127.

(Non-Patent Document 3) Bao, Yijun, and Thomas K. Gaylord. "Quantitative phase imaging method based on an analytical nonparaxial partially coherent phase optical transfer function." JOSA A 33.11(2016): 2125-2136.

(Non-Patent Document 4) Soto, Juan M., José A. Rodrigo, and Tatiana Alieva. "Label-free quantitative 3D tomographic imaging for partially coherent light microscopy." Optics express 25.14(2017): 15699-15712.

SUMMARY OF THE INVENTION

Embodiments describe a three-dimensional (3D) optical tomography method and apparatus using a partially coherent light and a multi-illumination pattern. More specifically, embodiments provide a technology for obtaining an accurate 3D refractive index image in simple optical measurement equipment using low coherence light (or partially coherent light) and not having a reference beam.

Embodiments provide a 3D optical tomography method and apparatus using a partially coherent light and a multi-illumination pattern, wherein light is made incident on a sample using several sheets of optimized patterns and thus refractive index tomography having an accurate value and shape is configured without the distortion of a 3D image.

Embodiments provide a 3D optical tomography method and apparatus using a partially coherent light and a multi-illumination pattern, which can accurately measure 3D refractive index information of a small sample using a simple image measurement apparatus not using interferometry, using common light having low coherence.

In an embodiment, a three-dimensional (3D) optical diffraction tomography method based on low coherence light and a multi-illumination pattern using a 3D optical diffraction tomography apparatus may include making light incident on a sample using a plurality of patterns, measuring, by an image measurement unit, different locations at different depth locations of the sample and measuring two-dimensional (2D) images of the sample, and reconstructing 3D refractive index information of the sample based on the different patterns and the 2D images obtained at the different depth locations.

The 3D optical diffraction tomography method may further include generating, by a light propagation unit positioned between the sample and the image measurement unit, a propagation of the light between the sample and the image measurement unit, before measuring the 2D images of the sample.

Making the light incident on the sample using the plurality of patterns may include determining patterns so that optical transfer function (OTF) are uniform as much as possible at respective spatial frequency locations, if at least three illumination patterns are used, intensity of the light is located at an outermost side of a spatial frequency coordinate system, and a final optical transfer function (OTF) is generated by combining patterns satisfying a condition in which the intensity of the light is decreased as the spatial frequency moves from a point defined as the outermost side to a center of the spatial frequency coordinate system.

Making the light incident on the sample using the plurality of patterns may include making the light incident on the sample using the plurality of patterns by controlling an incident pattern using a transmissive or reflective display or a device in which patterns are written.

Making the light incident on the sample using the plurality of patterns may include making the light incident on the sample using the plurality of patterns by controlling an incident pattern using the light incident on a fixed instrument at different angles.

Making the light incident on the sample using the plurality of patterns may include making the light incident on the sample using the plurality of patterns using a light-emitting diode (LED) array or a micro LED array with which an incident pattern controller for controlling the light and the patterns are integrated.

Reconstructing the 3D refractive index information of the sample based on the 2D images may include reconstructing the 3D refractive index information of the sample using a method of computing a 3D point spread function (PSF) based on amplitude and a phase and reconstructing v(x,y,z) =amplitude(x,y,z)+i*phase(x,y,z) based on 2D image i(x,y, z) information measured at different locations z.

In an embodiment, a three-dimensional (3D) optical diffraction tomography apparatus using low coherence light and a multi-illumination pattern may include an incident pattern controller configured to make light incident on a sample using a plurality of patterns, an image measurement unit configured to measure different locations at different depth locations of the sample and measure two-dimensional (2D) images of the sample, and a calculation unit configured to reconstruct 3D refractive index information of the sample based on the different patterns and the 2D images obtained at the different depth locations.

The 3D optical diffraction tomography apparatus may further include a light propagation unit positioned between the sample and the image measurement unit and configured to generate a propagation of the light between the sample and the image measurement unit.

The incident pattern controller may determine patterns so that optical transfer function (OTF) are uniform as much as possible at respective spatial frequency locations, if at least three illumination patterns are used, intensity of the light is located at an outermost side of a spatial frequency coordinate system, and a final OTF is generated by combining patterns satisfying a condition in which the intensity of the light is decreased as the spatial frequency moves from a point defined as the outermost side to a center of the spatial frequency coordinate system.

According to embodiments, the three-dimensional optical tomography method and apparatus using a partially coherent light and a multi-illumination pattern can be provided, which can accurately measure 3D refractive index information of a small sample using the simple image measurement apparatus not using interferometry, using common light having low coherence.

Furthermore, according to embodiments, 3D refractive index information of a transparent object, such as a biology cell which was difficult to be accurately measured using the existing technologies, can be easily and precisely measured. Accordingly, the present disclosure may be widely used in biology research and medical diagnosis fields without an additional sign.

DETAILED DESCRIPTION

Figure 1A:
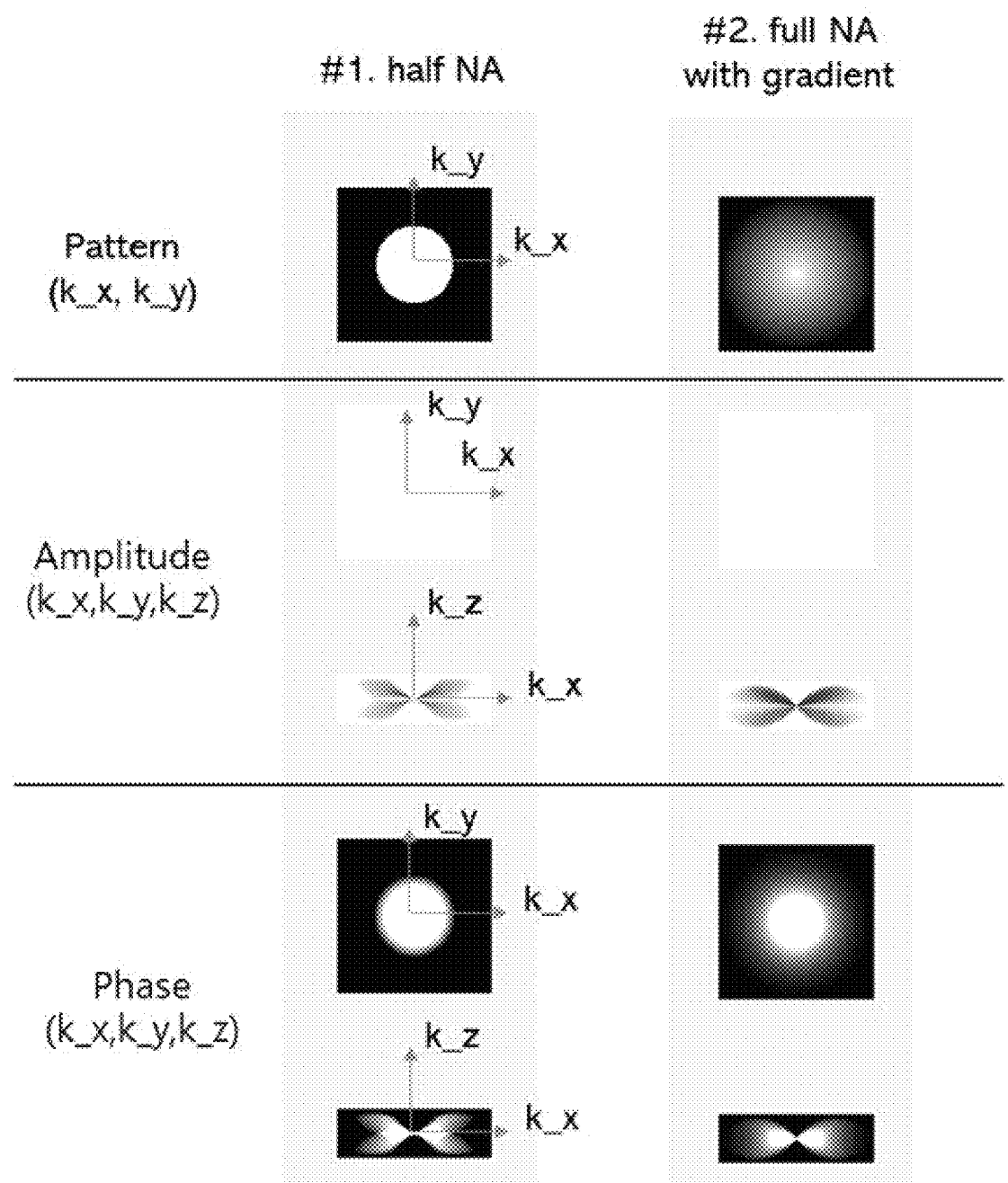
FIG. 1A is a diagram illustrating examples of the reconstruction of common low coherence three-dimensional (3D) microscope images.

Hereinafter, embodiments are described in detail with reference to the accompanying drawings. However, the described embodiments may be modified in various other forms, and the scope of the present disclosure is not restricted by the following embodiments. Furthermore, various embodiments are provided to more fully describe the present disclosure to a person having average knowledge in the art. The shapes, sizes, etc. of elements in the drawings may be exaggerated for a clear description.

The following embodiments provide a technology for obtaining an accurate three-dimensional (3D) refractive index image in simple optical measurement equipment using low coherence light (or partially coherent light) and not having a reference beam.

A problem of the existing technology, which was found through research, is that the optical transfer function (OTF) of an image system is not accurately incorporated in a two-dimensional (2D) information acquisition process for configuring a 3D image. Accordingly, severe information distortion may occur in measured and configured 3D image information. More specifically, in the existing method, common microscope light called a Kohler illumination is used as light incident on a sample. In this case, a 3D image is distorted because transfer efficiency is different for each configured 3D spatial frequency.

In order to overcome such a limit, the present embodiment is to make light incident on a sample using several sheets of optimized patterns and thus to configure refractive index tomography having an accurate value and shape without the distortion of a 3D image.

Embodiments relates to a technology for restoring a 3D refractive index image using low coherence light (or partially coherent light). More specifically, according to embodiments, 2D pattern light is used, and special pattern light capable of minimizing the distortion of the OTF is used.

According to the 3D image generation theory (i.e., Non-Patent Documents 2 and 3), a 3D object is configured with distribution amplitude (x,y,z) related to the absorbance of 3D light and a distribution phase (x,y,z) related to a refractive index. The 3D object is represented as "v(x,y,z)=amplitude(x,y,z)+i*phase(x,y,z)" as a complex number. If the 3D object is written in a camera using image equipment, such as a microscope, the intensity of an obtained light distribution may be represented like the following equation.

$$i(x,y,z)=b(x,y,z)+\text{amplitude}(x,y,z)\otimes \text{PSF\_A}(x,y,z)+ \text{phase}(x,y,z)\otimes \text{PSF\_P}(x,y,z) \quad (1)$$

In Equation 1, b indicates a background light intensity distribution. A symbol ⊗ indicates convolution. PSF_A(x,y,z) and PSF_P(x,y,z) are 3D point spread functions (PSF) based on amplitude and a phase, respectively.

A 3D image is reconstructed using several sheets of 2D intensity distribution images obtained at different locations z. Specifically, a 3D image may be reconstructed on a 3D space using Equation 2 obtained by performing a Fourier transform on Equation 1. If the Fourier transform is performed on Equation 1, Equation 1 may be represented like the following equation.

$$I(k\_x,k\_y,k\_z)=B(k\_x,k\_y,k\_z)+\text{Amplitude}(k\_x,k\_y,k\_z)\,H\_A(k\_x,k\_y,k\_z)+\text{Phase}(k\_x,k\_y,k\_z)\,H\_P(k\_x,k\_y,k\_z) \quad (2)$$

In Equation 2, B(k_x,k_y,k_z), amplitude(k_x,k_y,k_z), and Phase(k_x,k_y,k_z) are obtained by performing 3D Fourier transforms on b(x,y,z), amplitude(x,y,z), and phase (x,y,z), respectively. The upper case and the lower case may be distinctly represented.

When an optical microscope system is prepared, PSF_A(x,y,z) and PSF_P(x,y,z) are calculated and input depending on a configuration of the light and image acquisition unit of the optical microscope system. A 3D reconstruction process may be performed using a method of reconstructing v(x,y,z)=amplitude(x,y,z)+i*phase(x,y,z) through Equation 2 based on i(x,y,z) information measured at different locations z, respectively. In this case, from Equation 1 and Equation 2, it may be seen that quality of the 3D image reconstruction is determined by a shape of PSF_A(x,y,z) and PSF_P(x,y,z).

FIG. 1A is a diagram illustrating examples of the reconstruction of a common low coherence 3D microscope image. Furthermore, FIG. 1B is a diagram illustrating 3D reconstruction images of experimentally measured fine plastic beads of FIG. 1A.

FIG. 1A illustrates examples of the reconstruction of conventional common low coherence 3D microscope images and illustrates shapes of a 3D OTF based on each incident condition. In this case, amplitude and a phase may be reversed in all the drawings.

FIG. 1A illustrates the results of simulations and experiments when common incident light was used. The first case ("#1, half NA") of FIG. 1A illustrates a Kohler illumination if light incident on a sample was used in a common microscope, and is a case where the light was incident on a half numerical aperture (NA) based on the NA of an objective lens. In view of amplitude OTF and a phase OTF, it can be seen that a case where information is not measured for each spatial frequency and a case where information is distorted and reconstructed are many. Furthermore, the second case ("#2, full NA with gradient") of FIG. 1A is a case where light was incident on the full NA of an objective lens based on the NA of the objective lens.

Figure 1B:
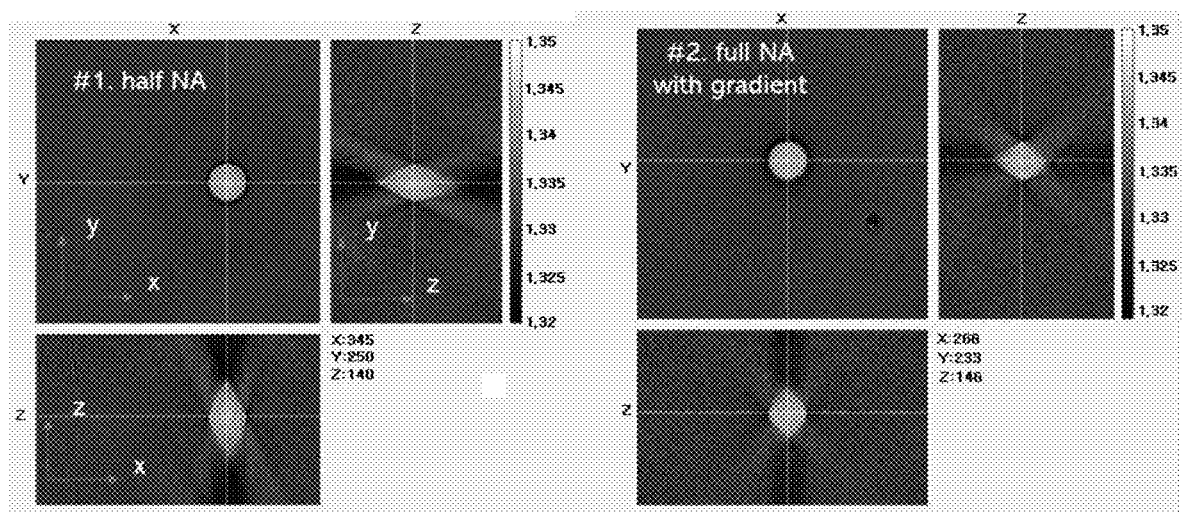
FIG. 1B is a diagram illustrating 3D reconstruction images of experimentally measured fine plastic beads of FIG. 1A.

If an image is obtained based on the simulations and experiments, results such as FIG. 1B may be obtained. That is, referring to FIG. 1B, 3D reconstruction images of experimentally measured fine plastic beads can be seen, and it can be seen that distortion corresponding to the 3D image occurs. In this case, the images may be obtained by putting oil into fine plastic beads (e.g., polystyrene bead) having a diameter of 3 um.

Figure 2A:
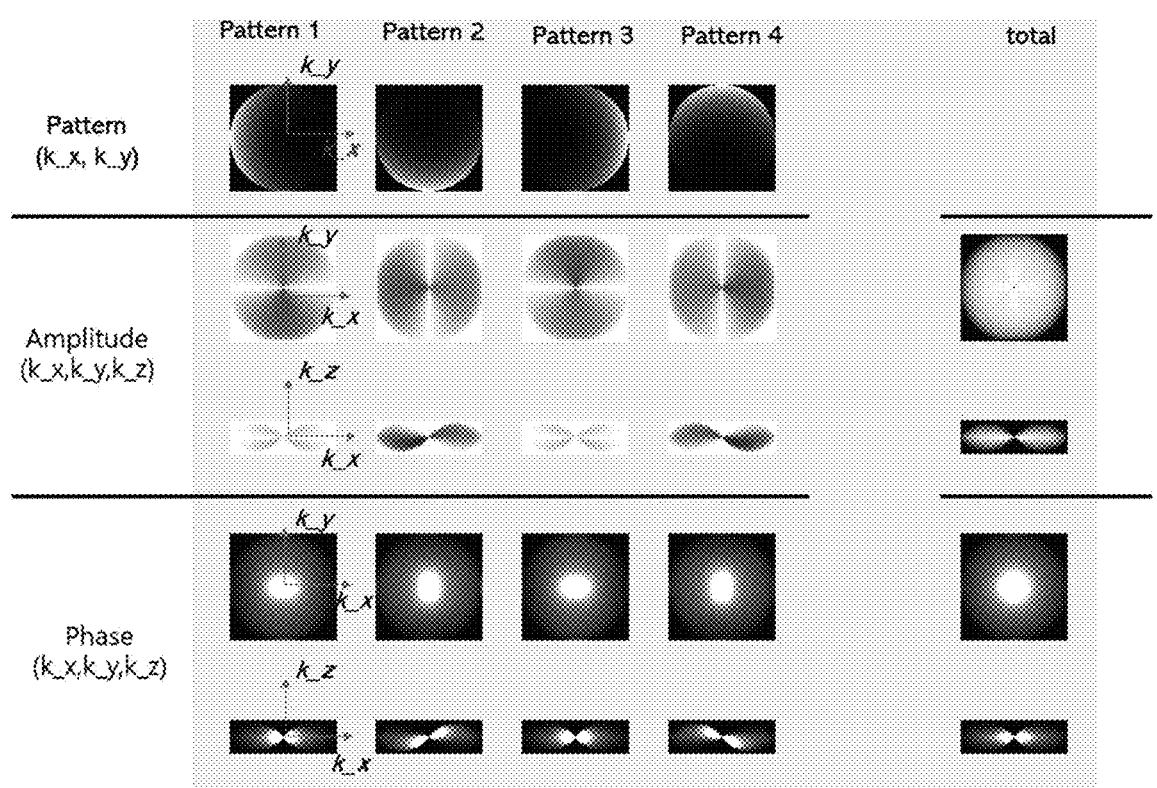
FIG. 2A is a diagram illustrating characteristics of several sheets of incident patterns according to an embodiment.
Figure 2B:
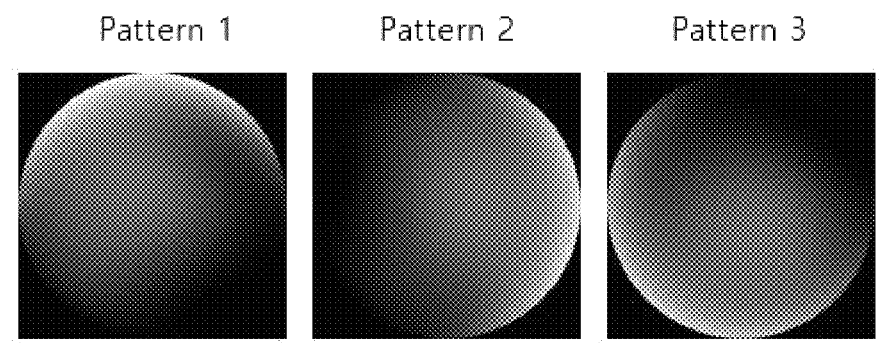
FIG. 2B is a diagram illustrating an example in which three incident patterns are used according to an embodiment.
Figure 2C:
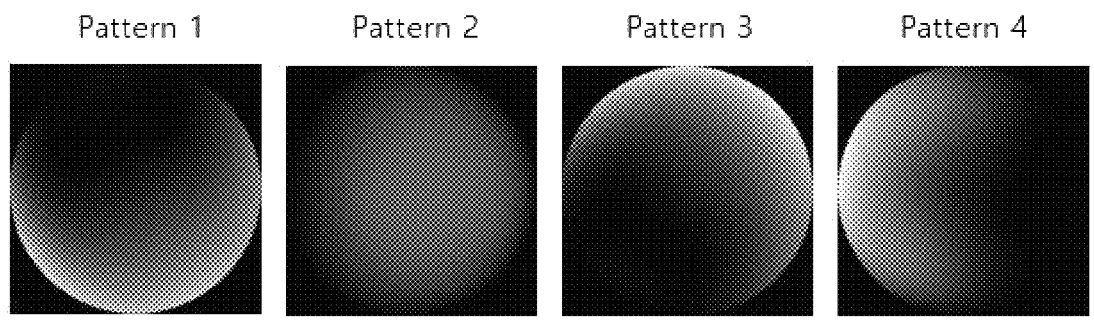
FIG. 2C is a diagram illustrating an example in which four incident patterns are used according to an embodiment.
Figure 2D:
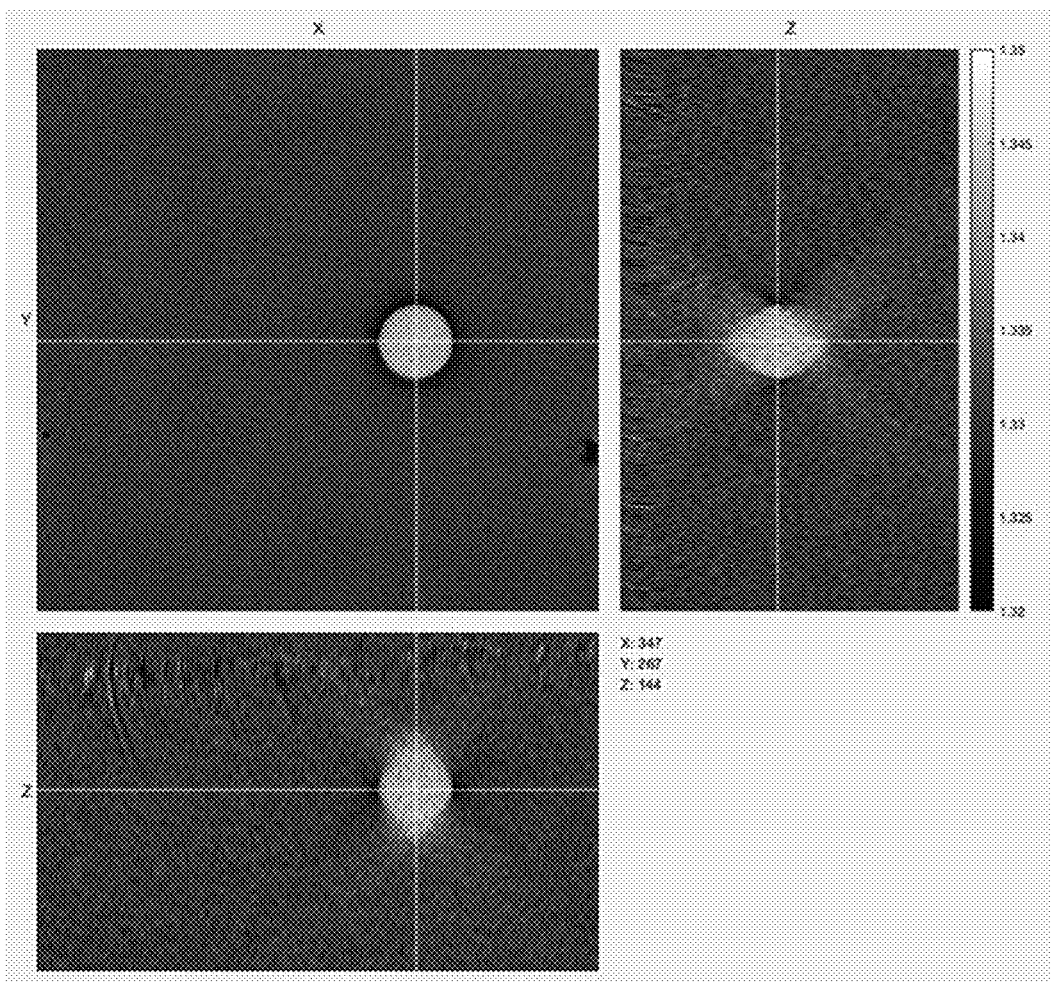
FIG. 2D is a diagram illustrating the results of 3D refractive index images obtained using several sheets of incident patterns calculated according to an embodiment.

FIG. 2A is a diagram illustrating characteristics of several sheets of incident patterns according to an embodiment. Furthermore, FIG. 2B is a diagram illustrating an example in which three incident patterns are used according to an embodiment. FIG. 2C is a diagram illustrating an example in which four incident patterns are used according to an embodiment. Furthermore, FIG. 2D is a diagram illustrating the results of 3D refractive index images obtained using several sheets of incident patterns calculated according to an embodiment.

According to the present embodiment, a 3D image is configured using several sheets of incident patterns specially computed so that 3D PSF PSF_A(x,y,z) and PSF_P(x,y,z) may have an identical situation based on amplitude and a phase. Characteristics of several sheets of incident patterns proposed in the present embodiment are illustrated in FIG. 2A. At least three light patterns are used, and have the following characteristics based on a spatial frequency coordinate system (k_x, k_y).

(1) At least three illumination patterns are used to simultaneously measure the real part and imaginary part of a refractive index. At least two illumination patterns are used to measure only the real part of a refractive index (i.e., if the absorption of light by a sample cannot be negligible).

(2) The location where the intensity of light is the greatest is the outermost side or center of the spatial frequency coordinate system.

(3) The intensity of light is decreased as the spatial frequency moves from the point defined in (2) to the place (i.e., center) where the spatial frequency is (0, 0). In this case, such a decrease tendency needs to be faster than a linear reduction.

(4) When the final optical transfer function (OTF) is generated by combining patterns that satisfy the conditions (1), (2), and (3), the patterns are determined so that OTF values are uniform as much as possible at respective spatial frequency locations.

In this case, three incident patterns may be used as the several sheets of incident patterns as illustrated in FIG. 2B or four incident patterns may be used as the several sheets of incident patterns as illustrated in FIG. 2C. FIG. 2D illustrates the results of 3D refractive index images obtained using the several sheets of incident patterns computed using a method proposed in the present embodiment. The illustrated patterns are examples of a pattern to which an embodiment is applied. In actual applications, a different combination of pattern that satisfies the conditions may be used.

It can be seen that the distortion and artifact of an image that were problematic in the results of the measurement using the existing method have been generally solved using the results of the measurement using the new method. In particular, as may be seen from a side view (i.e., x-z or x-y sectional view), it can be seen that the distortion of an image in a light-axial direction during the 3D reconstruction of the sample have been almost removed.

Figure 3A:
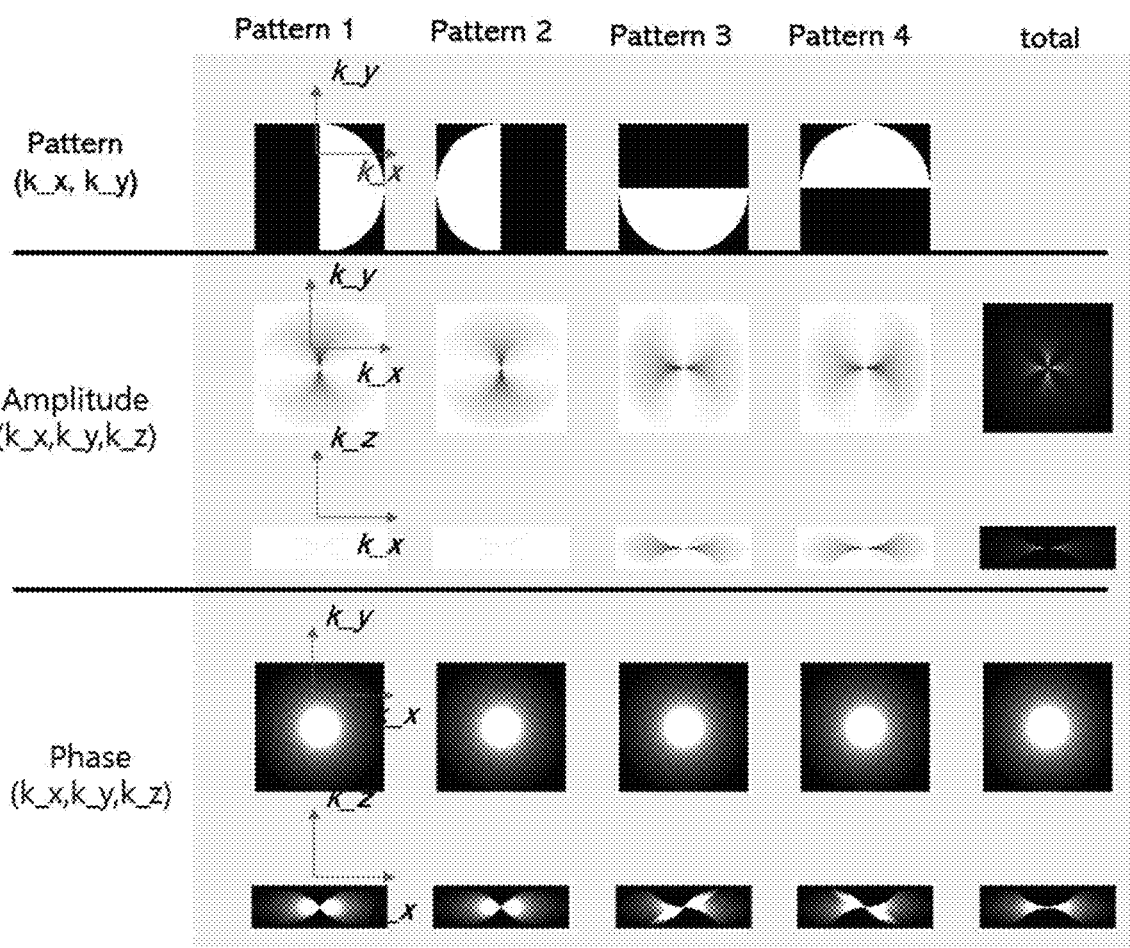
FIG. 3A is a diagram illustrating characteristics of incident patterns that do not satisfy conditions proposed in an embodiment.

FIG. 3A is a diagram illustrating characteristics of incident patterns that do not satisfy the conditions proposed in an embodiment. Furthermore, FIG. 3B is a diagram illustrating the results of 3D refractive index images obtained using an incident pattern that does not satisfy the conditions proposed in an embodiment.

Figure 3B:
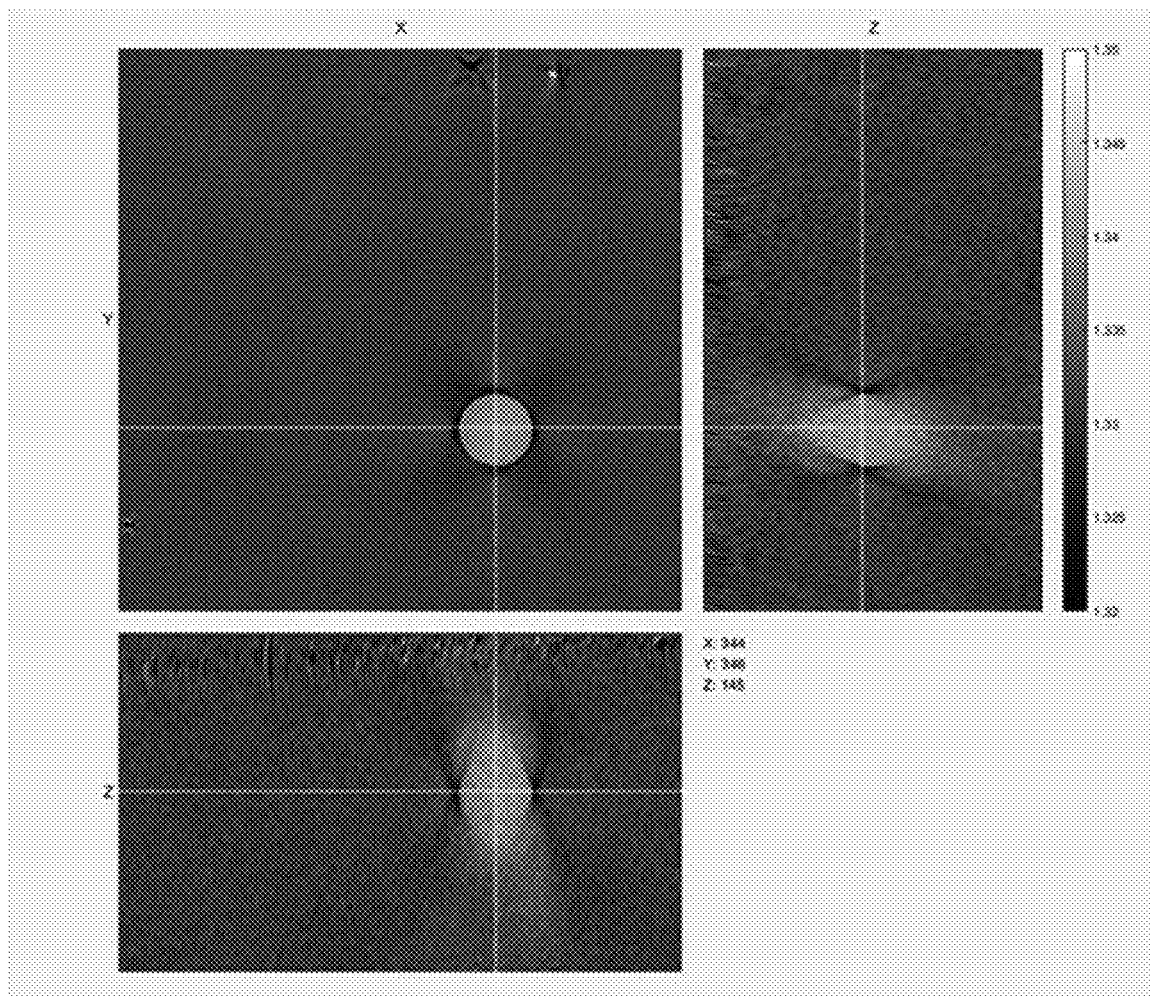
FIG. 3B is a diagram illustrating the results of 3D refractive index images obtained using an incident pattern that does not satisfy conditions proposed in an embodiment.

FIGS. 3A and 3B illustrate 3D refractive index images obtained in another incident pattern that does not satisfy the conditions proposed in the present embodiment. It can be seen that the distortion of the images are clear.

The method proposed in the present embodiment and the results of the 3D refractive index images obtained using the method may not be achieved using only several light patterns. For example, if a refractive index is reconstructed using several sheets of patterns each simply blocking only the half of light, more severe image distortion may occur. The reason for this is that although the several sheets of patterns are used, the 3D OTF space is not unfairly filled if simple patterns are used.

Figure 4:
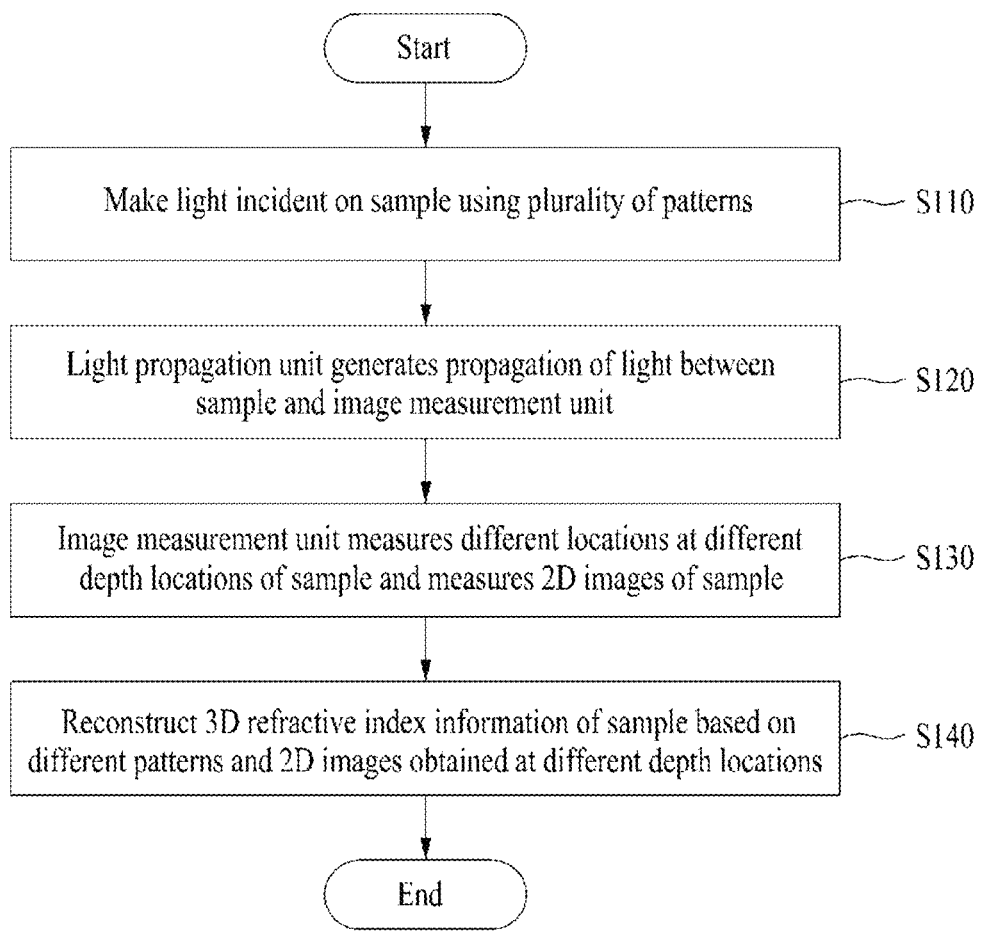
FIG. 4 is a flowchart illustrating a 3D optical diffraction tomography method according to an embodiment.

FIG. 4 is a flowchart illustrating a 3D optical diffraction tomography method according to an embodiment.

Referring to FIG. 4, the 3D optical diffraction tomography method based on low coherence light and a multi-illumination pattern using the 3D optical diffraction tomography apparatus according to an embodiment may include the step S110 of making light incident on a sample using a plurality of patterns, the step S130 of measuring, by an image measurement unit, measuring different locations at different depth locations of the sample and measuring 2D images of the sample, and the step S140 of reconstructing 3D refractive index information of the sample based on the different patterns and the 2D images obtained at the different depth locations.

Before the 2D images of the sample are obtained, the method may further include the step S120 of generating, by a light propagation unit positioned between the sample and the image measurement unit, the propagation of light between the sample and the image measurement unit.

Hereinafter, the steps of the 3D optical diffraction tomography method according to an embodiment are more specifically described.

The 3D optical diffraction tomography method according to an embodiment may be more specifically described using the 3D optical diffraction tomography apparatus according to an embodiment.

Figure 5:
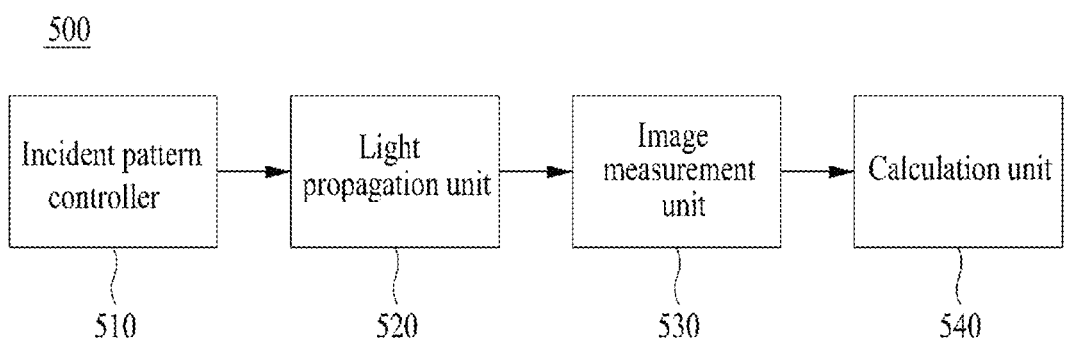
FIG. 5 is a block diagram illustrating a 3D optical diffraction tomography apparatus according to an embodiment.

FIG. 5 is a block diagram illustrating the 3D optical diffraction tomography apparatus according to an embodiment.

Referring to FIG. 5, the 3D optical diffraction tomography apparatus 500 according to an embodiment may include an incident pattern controller 510, an image measurement unit 530, and a calculation unit 540. In some embodiments, the 3D optical diffraction tomography apparatus 500 may further include a light propagation unit 520.

At step S110, the incident pattern controller 510 may make light incident on a sample using a plurality of patterns. The incident pattern controller 510 is an apparatus for controlling an incident pattern. In this case, the sample may be configured as a transmissive or reflective structure.

The incident pattern controller 510 may determine patterns so that optical transfer functions (OTFs) values of the patterns are uniform as much as possible at respective spatial frequency location, if at least three illumination patterns are used, the intensity of light is located at the outermost side of the spatial frequency coordinate system, and the final OTF of the pattern is generated by combining patterns that satisfy a condition in which the intensity of the light is decreased as the spatial frequency moves from the point defined as the outermost side to the center.

The incident pattern controller 510 may make light incident on a sample using a plurality of patterns by controlling an incident pattern using a transmissive or reflective display. For example, the transmissive controller may be configured using a liquid crystal display (LCD). For another example, the reflective controller may be configured using a digital micromirror device (DMD). For yet another example, the transmissive or reflective controller may be configured using a spatial light modulator.

The incident pattern controller 510 may make light incident on a sample using a plurality of patterns by controlling an incident pattern using a device in which patterns are written. For example, the incident pattern may be controlled by rotating or transferring at least one 2D extinction pattern that satisfies the aforementioned pattern conditions.

The incident pattern controller 510 may make light incident on a sample using a plurality of patterns by controlling an incident pattern using light incident on a fixed instrument at different angles. That is, in order to control the incident pattern, the incident pattern controller 510 may be configured to control light incident on the fixed instrument. For example, the incident pattern controller 510 may be configured to satisfy the aforementioned pattern conditions using light incident on a hemispherical fixed instrument at different angles.

Furthermore, the incident pattern controller 510 may make light incident on a sample using a plurality of patterns, using a light-emitting diode (LED) array or micro LED array with which the incident pattern controller 510 for controlling light and a pattern is integrated.

At step S120, the light propagation unit 520 is positioned between the sample and the image measurement unit 530, and may generate the propagation of light between the sample and the image measurement unit 530. The light propagation unit 520 is a device capable of generating the propagation of light between the sample and the image measurement unit 530 or an instrument capable of changing a focal distance between the sample and the image measurement unit 530.

At step S130, the image measurement unit 530 is configured to measure different locations at different depth locations of the sample, and may measure 2D images of the sample. For example, the image measurement unit 530 may be configured to move an objective lens for obtaining information, scattered by the sample, closer to or farther in the direction of the sample. Furthermore, the image measurement unit 530 may be configured to move the location of the sample closer or farther in the direction of the lens. Furthermore, the image measurement unit 530 may be configured to change a focal distance of the lens.

At step S140, the calculation unit 540 may reconstruct several sheets of obtained 2D images into a 3D refractive index image. The calculation unit 540 may reconstruct 3D refractive index information of the sample using Equation 2 based on the different patterns and the 2D images obtained at the different depth locations.

More specifically, the step of reconstructing the 3D refractive index information of the sample based on the 2D images may include reconstructing the 3D refractive index information of the sample using a method of calculating a 3D point spread function (PSF) based on amplitude and a phase and reconstructing "$v(x,y,z)=\text{amplitude}(x,y,z)+i*\text{phase}(x,y,z)$" using Equation 2 based on 2D image $i(x,y,z)$ information measured at different locations z.

Figure 6:
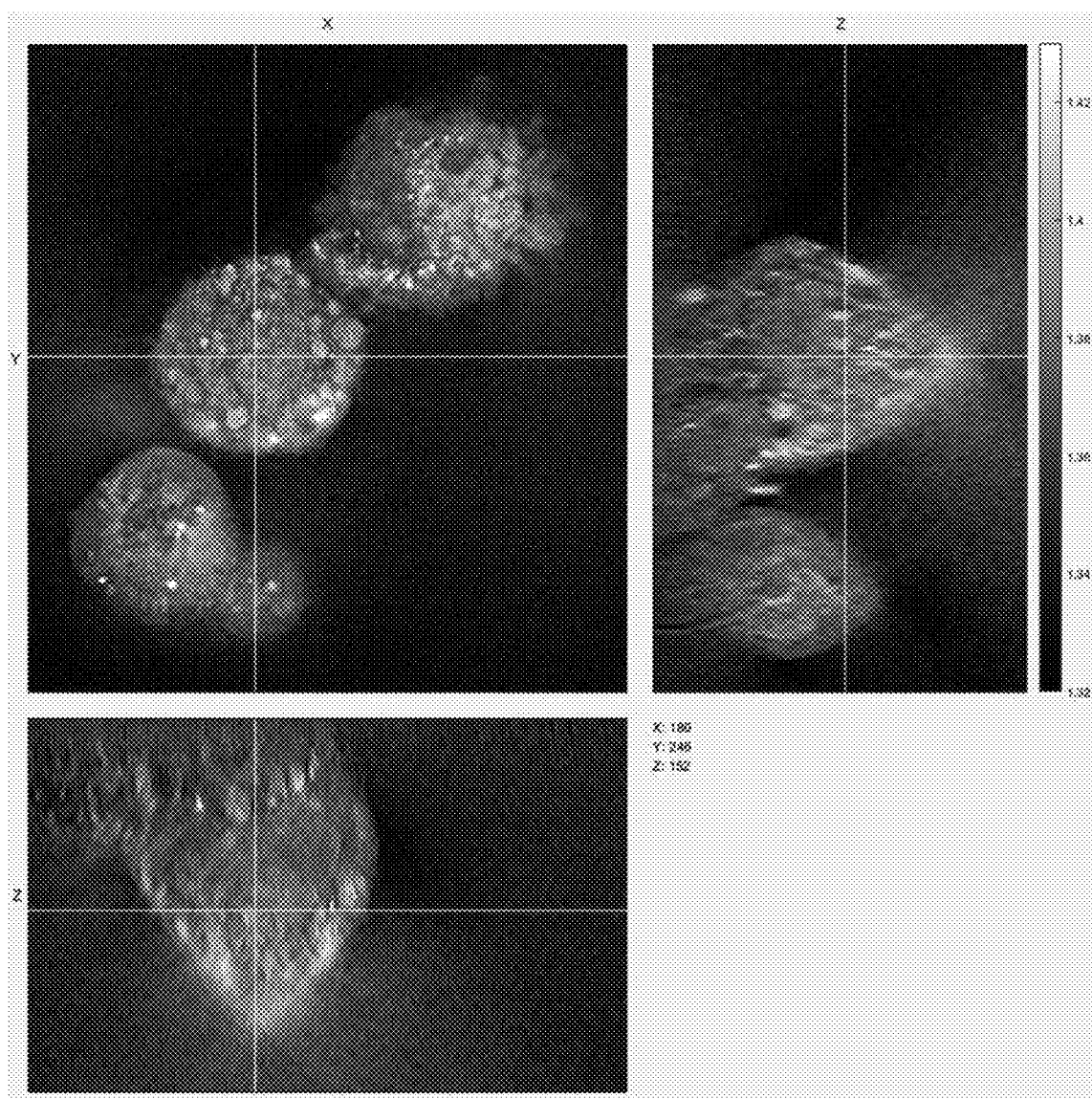
FIG. 6 is a diagram illustrating 3D refractive index images of cancer cells measured according to an embodiment.

FIG. 6 is a diagram illustrating 3D refractive index images of cancer cells measured according to an embodiment. FIG. 6 illustrates examples of 3D refractive index images of cancer cells obtained according to an embodiment.

According to embodiments, the three-dimensional optical tomography method and apparatus using a partially coherent light and a multi-illumination pattern can be provided, which can accurately measure 3D refractive index information of a small sample using the simple image measurement apparatus not using interferometry, using common light having low coherence.

Furthermore, according to embodiments, 3D refractive index information of a transparent object, such as a biology cell which was difficult to be accurately measured using the existing technologies, can be easily and precisely measured.

Accordingly, the present disclosure may be widely used in biology research and medical diagnosis fields without an additional sign.

The aforementioned apparatus may be implemented as a hardware component, a software component and/or a combination of them. For example, the apparatus and components described in the embodiments may be implemented using one or more general-purpose computers or special-purpose computers, for example, a processor, a controller, an arithmetic logic unit (ALU), a digital signal processor, a microcomputer, a field programmable gate array (FPGA), a programmable logic unit (PLU), a microprocessor or any other device capable of executing or responding to an instruction. The processing apparatus may perform an operating system (OS) and one or more software applications executed on the OS. Furthermore, the processing apparatus may access, store, manipulate, process and generate data in response to the execution of software. For convenience of understanding, one processing apparatus has been illustrated as being used, but a person having ordinary skill in the art may understand that the processing apparatus may include a plurality of processing elements and/or a plurality of types of processing elements. For example, the processing apparatus may include a plurality of processors or a single processor and a single controller. Furthermore, other processing configurations, such as a parallel processor, are also possible.

Software may include a computer program, code, an instruction or a combination of one or more of them and may configure a processor so that it operates as desired or may instruct processors independently or collectively. The software and/or data may be embodied in any type of a machine, component, physical device, virtual equipment, or computer storage medium or device in order to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure alone or in combination. The program instructions stored in the medium may be specially designed and constructed for the present disclosure, or may be known and available to those skilled in the field of computer software. Examples of the computer-readable storage medium include magnetic media such as a hard disk, a floppy disk and a magnetic tape, optical media such as a CD-ROM and a DVD, magneto-optical media such as a floptical disk, and hardware devices specially configured to store and execute program instructions such as a ROM, a RAM, and a flash memory. Examples of the program instructions include not only machine language code that is constructed by a compiler but also high-level language code that can be executed by a computer using an interpreter or the like.

As described above, although the embodiments have been described in connection with the limited embodiments and drawings, those skilled in the art may modify and change the embodiments in various ways from the description. For example, proper results may be achieved although the above descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and equivalents of the claims belong to the scope of the claims.

What is claimed is:

1. A three-dimensional (3D) optical diffraction tomography method based on low coherence light and a multi-illumination pattern using a 3D optical diffraction tomography apparatus, the method comprising:
making light incident on a sample using a plurality of patterns;
measuring, by an image measurement unit, different locations at different depth locations of the sample and measuring two-dimensional (2D) images of the sample; and
reconstructing 3D refractive index information of the sample based on the different patterns and the 2D images obtained at the different depth locations,
wherein making the light incident on the sample using the plurality of patterns comprises determining patterns so that optical transfer function (OTF) are uniform as much as possible at respective spatial frequency locations, if at least three illumination patterns are used, intensity of the light is located at an outermost side of a spatial frequency coordinate system, and a final OTF is generated by combining patterns satisfying a condition in which the intensity of the light is decreased as the spatial frequency moves from a point defined as the outermost side to a center of the spatial frequency coordinate system.

2. The 3D optical diffraction tomography method of claim 1, further comprising generating, by a light propagation unit positioned between the sample and the image measurement unit, a propagation of the light between the sample and the image measurement unit, before measuring the 2D images of the sample.

3. The 3D optical diffraction tomography method of claim 1, wherein making the light incident on the sample using the plurality of patterns comprises making the light incident on the sample using the plurality of patterns by controlling an incident pattern using a transmissive or reflective display or a device in which patterns are written.

4. The 3D optical diffraction tomography method of claim 1, wherein making the light incident on the sample using the plurality of patterns comprises making the light incident on the sample using the plurality of patterns by controlling an incident pattern using the light incident on a fixed instrument at different angles.

5. The 3D optical diffraction tomography method of claim 1, wherein making the light incident on the sample using the plurality of patterns comprises making the light incident on the sample using the plurality of patterns using a light-emitting diode (LED) array or a micro LED array with which an incident pattern controller for controlling the light and the patterns are integrated.

6. The 3D optical diffraction tomography method of claim 1, wherein reconstructing the 3D refractive index information of the sample based on the 2D images comprises reconstructing the 3D refractive index information of the sample using a method of computing a 3D point spread function (PSF) based on amplitude and a phase and reconstructing $v(x,y,z) = \text{amplitude}(x,y,z) + i * \text{phase}(x,y,z)$ based on 2D image $i(x,y,z)$ information measured at different locations z.

7. A three-dimensional (3D) optical diffraction tomography apparatus using low coherence light and a multi-illumination pattern, comprising:
- an incident pattern controller configured to make light incident on a sample using a plurality of patterns;
- an image measurement unit configured to measure different locations at different depth locations of the sample and measure two-dimensional (2D) images of the sample; and
- a calculation unit configured to reconstruct 3D refractive index information of the sample based on the different patterns and the 2D images obtained at the different depth locations, wherein the incident pattern controller determines patterns so that optical transfer function (OTF) are uniform as much as possible at respective spatial frequency locations, if at least three illumination patterns are used, intensity of the light is located at an outermost side of a spatial frequency coordinate system, and a final OTF is generated by combining patterns satisfying a condition in which the intensity of the light is decreased as the spatial frequency moves from a point defined as the outermost side to a center of the spatial frequency coordinate system.

8. The 3D optical diffraction tomography apparatus of claim 7, further comprising a light propagation unit positioned between the sample and the image measurement unit and configured to generate a propagation of the light between the sample and the image measurement unit.

* * * * *